United States Patent [19]
Cohn

[11] Patent Number: 5,499,010
[45] Date of Patent: Mar. 12, 1996

[54] BRAKING LIGHT SYSTEM FOR A VEHICLE

[75] Inventor: Theodore E. Cohn, Kensington, Calif.

[73] Assignee: The Regents of the University of California, Oakland, Calif.

[21] Appl. No.: 232,486

[22] Filed: Apr. 25, 1994

[51] Int. Cl.⁶ .................................................. B60Q 1/44
[52] U.S. Cl. .......................................... 340/479; 340/464
[58] Field of Search .................................. 340/479, 464, 340/467, 471, 463, 468; 187/271, 282; 200/61.89, 86.5

[56] References Cited

U.S. PATENT DOCUMENTS

| | | | |
|---|---|---|---|
| 3,629,815 | 12/1971 | Hattwig | 340/479 |
| 3,903,501 | 9/1975 | Greenlee et al. | |
| 4,556,862 | 12/1985 | Meinershagen | 340/479 |
| 4,663,609 | 5/1987 | Rosario | 340/479 |
| 4,894,640 | 1/1990 | Beasley et al. | 340/479 |
| 4,896,137 | 1/1990 | Lee et al. | 340/479 |
| 4,920,330 | 4/1990 | Plozner | 340/479 |
| 4,933,666 | 6/1990 | Maple | 340/479 |
| 4,983,952 | 1/1991 | Athalye | 340/479 |
| 4,983,953 | 1/1991 | Page | 340/479 |
| 5,172,095 | 12/1992 | Scott | 340/479 |

OTHER PUBLICATIONS

"Relative Efficiency for Detection of an Apparent Motion Stimulus", B. G. Gros et al, one-page Abstract, distributed by mail possibly before apr. 24, 1993.
"What Does the Eye See Best?", Andrew B. Watson et al, Letters to Nature, vol. 302, Mar. 31, 1983, pp. 419–422.
"Perceptual Latencies to Sinusoidal Gratings", Uwe Lupp, et al., Vision Res., vol. 16, pp. 969–972, Pergamon Press, Printed in Great Britain.
"Optic Nerve Damage in Human Glaucoma", Harry A. Quigley, et al, Arch Opthalmol 1982, 100, pp. 135–146.
"Cat and Monkey Retinal Ganglion Cells and Their Visual Functional Roles", Robert Shapley, et al TINS, May 1986, pp. 229–235.
"Human Perception and Performance", Kenneth R. Boff et al, Engineering Data Compendium, vol. III 1988, Wright–Patterson Air Force Base, pp. 1842–1890.

*Primary Examiner*—John K. Peng
*Assistant Examiner*—Nina Tong
*Attorney, Agent, or Firm*—Flehr, Hohbach, Test, Albritton & Herbert

[57] ABSTRACT

Apparent motion is created in an object to stimulate rapid M cell response in an observer's visual system. In one embodiment, a vehicle is equipped with at least left and right pairs of brake lights spaced apart about 1 to 60 minutes of visual angle at the viewing distance. Vehicle braking activates the innermost of each pair of lights for duration T1, and after a duration T2, the outermost of each pair of lights is activated for the duration of the braking action. T1 is determined by luminous energy intensity from the innermost brake lights, and for incandescent lights is in the range of about 5 ms to about 50 ms. Duration T2 is selected to preclude an overlap in the observer's visual system between response to the end of the first-activated light, and the response commencing with the start of the second-activated light. For incandescent lights, T2 is in the range from about zero to about 50 ms. An observer rapidly perceives the brake lights as looming closer, due to the inward-to-outward sweeping visual image that enhances salience. Because the observer's M cells appear to be primarily stimulated by the luminous energy, the observer can react more rapidly to the braking action than to conventional brake lights.

12 Claims, 4 Drawing Sheets

BRAKING LIGHT SYSTEM FOR A VEHICLE

FIELD OF THE INVENTION

This invention relates to visual perception of lights used for display and warning, and more particularly to a method and apparatus for improving visual perception of such lights, and for ophthalmic disease testing.

BACKGROUND OF THE INVENTION

Lights are often used to display information, including information warning of a potentially dangerous condition. For example, brake lights on a motor vehicle are intended to alert those following that the vehicle in front is slowing or has stopped. Aircraft wing-tip strobe lights are intended to alert other pilots to the presence and direction of the aircraft. Lights are often used with machinery to provide warnings, for example, an automobile dashboard light that turns on to warn a motorist of low tire pressure, low brake pressure, and the like (so-called "telltale" lights). Lights are often used to warn of a stationary hazard, e.g., a flashing hazard light unit placed near an open hole in a roadway.

As used herein, the terms "light" or "light source" denote a source of luminous energy. Thus, "light" or "light source" can include, without limitation, incandescent bulbs, gas discharge tubes, fluorescent lamps, cathode ray tubes, liquid crystal displays, lasers, as well as solid state light-emitting-diodes ("LEDs").

When used as a warning device, a light should be perceived by an observer at the earliest possible moment. By "perceive", it is meant that an observer not only experiences a sensation due to the luminous energy from the light, but that the luminous energy immediately attracts the observer's attention. Thus, motor vehicle brake lights should, ideally, operate such that a motorist following perceives the luminous energy from the lights, recognizes that braking has occurred, and immediately begins evasive action, e.g., braking and/or steering. If the following vehicle is travelling at 55 mph, in one second 80' or 24 m will be covered. At that speed, if the vehicle in front suddenly brakes, or if a stationary hazard is suddenly encountered, a delay of perhaps only 50 ms in responding to the brake or warning light may determine whether a collision or a near miss results. In short, it is desired that an observer not merely "see" another vehicle's brake lights, or hazard warning lights, but that the observer perceive with minimal delay that the object ahead is looming ever closer.

Of course environmental degradation can interfere with the ability of observer to perceive warning or hazard lights. For example, it may be raining, the air may be foggy or dusty, there may be dust on the braking vehicle's brake lights or on the following vehicle's windshield. Further, the intensity of luminous energy from the brake lights might be diminished, perhaps from increased wiring resistance due to corrosion. All of these effects tend to veil the brake or warning light.

Dynamic looming visual information is also important in aviation. Federal law dictates that aircraft be provided with warning wing-tip lights that flash in unison, typically with a repetition rate of about one to two flashes per second. U.S. Pat. No. 3,903,501 to Greenlee et al. discloses the use of left wing and right pairs of for ward-facing wing tip lights that are used with left and right wing rearward-facing wing tip lights. On each wing, one of the pair of lights flashes synchronously with the corresponding rearward-facing light and approximately 175 ms later, the remaining light in each pair is flashed. The resultant double flashing pattern is stated to improve collision avoidance. It appears that Greenlee et al. would function equally well using a single for ward-facing light in each wing tip that flashes in synchronism with the rearward-facing light and flashes again 175 ms later. However, given the age of Greenlee et al., it is possible that gas discharge tube aircraft lights available at the time were not fast enough to double flash within 175 ms.

Even when looming type information is not critical, rapid recognition of luminous energy from a warning light can still be important. For example, if a dashboard mounted flashing LED that warns of low brake pressure or low tire pressure is not perceived in time by the motorist, damage to the motor vehicle can result. Similarly, lights may be used to demarcate highway lane edges. Future highways contemplated under the Intelligent Vehicle Highway System ("IVHS"), will have dramatically lessened lane widths. Thus, safe use of such future highways dictates that warnings of incursion by a vehicle upon the lane edge be heeded instantaneously.

Having described some general applications for warning lights, the physiology of visual detection will now be described briefly.

The sense of sight generally involves perception of form, color, size, movement and distance of objects. Stimuli in the form of visible luminous energy rays enter the eyes of an observer and form images on the retina. Cells in the retina absorb the luminous energy rays, are altered thereby, and generate electrical signals. Some of these signals are known to lead to nerve responses in subsequent neural ganglion cells. The axon portion of the ganglion cells carries information in the form of electrical impulses through optic nerve fibers to the lateral geniculate nucleus, and then to the visual cortex region of the brain. The visual cortex includes a projection region having a map-like correspondence to points on the retina, and thus to points in visual space.

Researchers generally classify the retinal ganglion cells as projecting to relatively large magnocellular cells ("M cells") or to smaller parvocelluar cells ("P cells") of the lateral geniculate. Especially relevant to the present invention, retinal M cells have a thicker axon than do P cells, which thickness permits neural impulses from M cells to travel more quickly to the brain than impulses from P cells. M cells also respond well to visual stimuli that are rapidly turned on and off, and to moving stimuli.

Thus, it is known in the relevant art that M cells have better function than P cells for recognizing transient visual stimuli, especially rapidly moving objects. It is also interesting to note that victims of certain ophthalmic disease, e.g., glaucoma, appear to initially suffer a degradation of M cell function. However, outside of the research laboratory, an effective procedure for testing for the onset of glaucoma by presenting a patient with stimuli intended to elicit M cell response is not yet in standard practice.

In summary, there is a need for a method and apparatus to enhance warning or hazard light visibility, to hasten viewer perception of such lights, and to improve salience. Because the human visual system appears to respond more rapidly to perceived object movement than to a stationary object, such method and apparatus preferably should stimulate and elicit such a response. In a dynamic warning application, preferably the light source should present a looming image that enhances and hastens the viewer's perception of approaching danger. Further, even in non-warning or hazard environments, there is a need for a visual display having an enhanced likelihood of capturing even a casual viewer's attention. Moreover, it is desirable to provide a warning signal whose visibility is resistant to the sensitivity-lowering effects of blur. Finally, there is a need for a method and apparatus to promote earlier detection of eye disease such as glaucoma that initially attacks a patient's M cells.

The present invention provides such methods and apparatuses.

SUMMARY OF THE PRESENT INVENTION

The present invention recognizes that the human visual system responds more rapidly and more sensitively to an object perceived to be in motion, than to the same object perceived to be at rest. The present invention creates apparent motion in an object, which perception appears to stimulate rapid M cell response in an observer's visual system. Further, by using sequentially operated pairs of paired lights, an apparent motion that enhances salience is created, resulting in a looming image that provides positional and directional information, readily perceived by an observer as representing a potential hazard.

A first embodiment creates apparent motion and enhances salience in brake lights used on motor vehicles. The vehicle rear brake lights comprise a left pair and right pair of lights. Upon braking, the innermost of each light pair is turned on for a brief interval T1, turned off, and after a short interval T2, the outermost of each light pair is turned on for as long as the brake pedal is depressed. An observer viewing the sequence of stimuli from the light sources perceives apparent motion. This perception appears to travel to the observer's brain rapidly via M cell axons rather than more slowly as would be the cause if P cell response were relied upon. Further, because the luminous energy from the light sources appears to sweep inward-to-outward, a salient or looming image is perceived. As a result, an observer (for example, a following motorist), perceives and responds more rapidly to the braking than if a conventional brake light system were used.

The duration T1 during which the innermost brake lights are on depends upon the intensity of the luminous energy, being perhaps 5 ms to 50 ms for energy from incandescent light sources, and being perhaps 1 µs or less for high intensity strobe or laser light sources. The duration T2 depends upon the turn-on, turn-off speed of the light sources relative to the duration of the perceived visual effects from the first-activated light source upon the observer's nervous system. Duration T2 must be sufficiently long such that the effects from the first-activated light source upon an observer's nervous system end before the second-activated light source is turned on. This prevents an overlap between the perceived effects of the light sources, which overlap could degrade salience. In practice, T2 may be essentially zero for incandescent light sources, and is perhaps 10 ms to 150 ms for strobe, LED, and laser light sources, and more preferably 10 ms to 100 ms.

Other embodiments use a repetitive flashing light source pattern to more rapidly attain an observer's attention and M cell response. Left and right aircraft wing-tip strobe light may be sequentially operated to stimulate a viewer's M cells and to visually convey information as to a desired evasive course of movement. One wing-tip strobe light is turned on for time T1, after an interval T2, the other wing-tip strobe light is turned on for an interval T3, and after a duty-cycle determining interval T4, the sequence is repeated continuously. T1 and T3 are preferably equal and are typically 1 µs or so, as determined by the intensity of the luminous energy from the wing-tip light source. Interval T2 is determined to preclude significant response overlap, and is in the 10 ms to 100 ms range.

A pair of light sources may be activated sequentially in an automobile dashboard warning system to more rapidly attain an observer's response. A plurality of such light source pairs may be used, for example to spell out a word in a warning or advertising sign, to outline or to define a warning symbol, an arrow for example, or other indicia.

Another embodiment is used for medical detection of eye disease and stimulates a patient's visual system with rays from a pair of closely spaced apart light sources that are operated in sequence. The sequentially generated luminous energy from these light sources elicits response primarily from the patient's M cells. This promotes early detection of diseases such as glaucoma that initially degrade M cell response.

In summary, the various embodiments of the present invention shares several characteristics in eliciting an M cell response in an observer. In each embodiment the light sources are spaced apart a distance corresponding to about 1 minute to about 1 degree of visual angle at the viewing distance of concern, with about 5 to 30 minutes of visual angle preferred. The time duration T1 during which the first-activated light source is on is determined by the intensity of the luminous energy provided by such light source, T1 being short for high intensity light sources (e.g., strobe lights), and being longer for lower intensity light sources (e.g., incandescent lights). The time interval T2 between activation of the first and second activated light sources in each embodiment is made sufficiently long to preclude an overlapping of the visual effects remaining from the first-activated light source and the visual effects beginning from the second-activated light source. In continuously flashing embodiments, the second-activated light source is on for a time T3 that is determined by the intensity of the luminous energy from this source, and may in fact equal time T1. A time T4 is determined according to desired duty cycle.

Other features and advantages of the invention will appear from the following description in which the preferred embodiments have been set forth in detail, in conjunction with the accompanying drawings.

DETAILED DESCRIPTION OF THE PREFERRED EMBODIMENTS

Figure 1A:
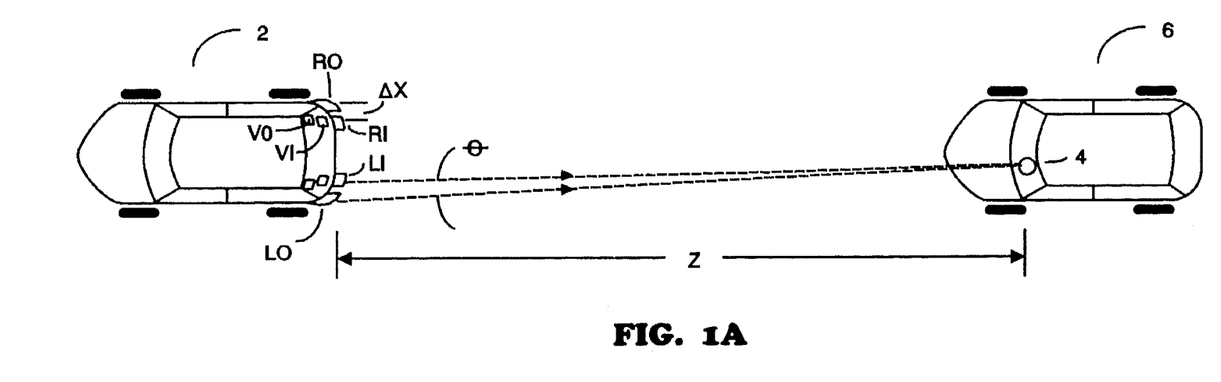
FIG. 1A is a plan view of a motor vehicle equipped with brake lights, according to the present invention.

FIG. 1A shows a preferred dynamic looming embodiment of the present invention, wherein braking of a first motor vehicle 2 is made more rapidly perceivable to an observer 4. FIG. 1A shows observer 4 operating a second motor vehicle 6 a distance Z behind the first motor vehicle.

The first vehicle 2 is equipped with a left pair of brake lights (e.g., brake light sources), denoted LO (for left-outer) and LI (for left-inner) and a right pair of brake lights, denoted RO and RI. According to the present invention, when the brake pedal of vehicle 2 is depressed, the inner brake lights LI and RI are turned on for a time T1 and are then extinguished, and after a time T2 the outer brake lights LO and RO are turned on and remain on for as long as the brake pedal is depressed. Lights LO and RO are caused to remain on because applicable highway regulations prohibit continuously flashing brake lights.

Preferably T1 is about 5 ms to 50 ms, with T1≈10 ms preferred, where the brake lights are incandescent devices. Time T2 should be sufficiently long that the effects of the luminous energy from the innermost brake light source upon an observer's nervous system substantially end before the effects of the outermost light sources commence. However incandescent light sources turn on and off more slowly than the visual nervous system response. Thus, in practice, T2 may be essentially zero, e.g., the outermost lights LO, RO may be turned on as the innermost lights LI, RI are turned off. It is important, however, that salience not be degraded by creating a perceived overlap of activated adjacent lights RI-RO, or LI-LO, caused by too short an interval T2. For incandescent lights, T2 may be as long as perhaps 50 ms.

The human eye perceives a burst of luminous energy by integrating the intensity of this energy over the burst duration. This implies that the smallest duration T1 during which the first-initiated light source is turned on is a function of the intensity of the luminous energy provided. Thus, if the brake lights were gas discharge strobe units that provide a high intensity burst of luminous energy, it would suffice for T1 to be on the order of microseconds, or less. On the other hand, motor vehicle brake lights are typically incandescent with less output intensity, and thus require an on time of perhaps 5 ms to 50 ms, according to the present invention. It will be appreciated that LO, RO, LI, RI need not be the same type devices. The innermost lights RI, LI are on only briefly, and may be faster-acting discharge type lights, whereas the outermost lights RO, LO can be conventional incandescent devices. In practice, it is preferred that the effective intensity of luminous energy provided by the light sources are within a range of about 200% to 300% of each other.

The time interval T2 is a function of the speed with which the light sources can be turned on and off, relative to the duration of the perceived visual effect from the first-activated light upon the observer's nervous system. For example, if the light sources were high speed devices such as lasers or strobe lights, the preferred range of T2 would be relatively long, for example from 5 ms to perhaps 150 ms, or longer. Were T2 significantly shorter, the second-activated light source would turn on so rapidly, that its visual contribution would be perceived while the observer's visual nervous system was still experiencing the effect of the off-turning first-activated light source. Thus, in the various embodiments of the present invention, the T2 interval should be sufficiently long so that rays of luminous energy from the second-activated light source are not perceived as overlapping in time the effect of rays perceived from the first-activated light source.

For incandescent light sources, applicant believes T1≈10 ms, 0≦T2≦100 ms will result in a sequential operation of brake lights that more certainly stimulates the M cells of observer 4, thus hastening the perception process. What apparently occurs is that the horizontal "inward-to-outward" visual pattern produced by the brake lights creates a salient or looming visual effect that causes observer 4 to perceive the rear of vehicle 2 as getting larger and thus closer. Observer 4's brain recognizes a looming pattern as presenting a potential danger, and observer 4 then knows to brake, steer or otherwise control vehicle 6 to avoid colliding with the looming object ahead. It is also possible that the described sequential operation of the brake lights enhances observer perception due to other factors as well. For example, it is possible that the described sequential operation presents a color spectrum that is more effectively perceived, although in a manner not presently known.

In fact, observer 4 will begin to respond sooner than if vehicle 2 were not equipped with brake lights sequentially operated according to the present invention. Of course, more than two pairs of brake lights may be activated to signal braking. A third light VI, VO might be disposed adjacent the rear-window region of vehicle 2, preferably spaced apart vertically. When braking, the innermost light in each light pair would be turned on, then off, after which the outermost light of each light pair would be turned on for the duration of the braking. The resultant stimulus presents an image that appears to loom horizontally and vertically.

It is understood from FIG. 1A while other activation sequences are possible, they are not desirable. For example, if the outer brake lights RO, LO were first turned on, then off, and then the inner brake lights RI, LI were turned on, vehicle 2 would falsely appear to be receding, or anti-looming. If the leftmost light in each pair LO, RI were turned on, then off and then the right most light in each pair LI, RO were turned on (or vice versa), a false swerving image of vehicle 2 would be perceived by observer 4.

Adjacent lights RI, RO and LI, LO preferably are separated a distance ΔX that corresponds to about 1 minute (1/60°) to about 1° of visual angle at the distance of concern, Z, and preferably 5 to 30 minutes (1/12° to 1/2°) of visual angle. For example, in a motor vehicle dynamic warning environment, such as shown in FIG. 1A, at 55 mph, each vehicle covers 80' (24 m) in one second. Typically, it is assumed that a motor vehicle operator can react (e.g., to an object or hazard in the road) and begin to brake in perhaps one second. Using this as a guideline, the distance of concern Z is about 100'and as Z decreases, it is even more important that observer 4 rapidly perceive that vehicle 2 is braking, and begin to control vehicle 6 appropriately.

From trigonometry, it follows that ΔX=Ztanθ. Thus, for Z≈100', and for θ≈0.08° to about 0.5°, ΔX preferably should be in range 0.14' (1.7" or 4.3 cm) to about 0.9' (10.5" or 26.6 cm). Typically, the rear light assembly for motor vehicles can easily accommodate left and right pairs of brake lights, wherein the members of each pair (e.g., RO, RI and LO, LI) are spaced apart a few inches.

Ideally, the intensity of each light source RO, RI, LO, LI is as high as is practical, in that a more intense light stimulus will be more readily and rapidly perceived under a given set of conditions than a less intense light stimulus. As a practical matter, however, federal and/or local regulations may establish upper limits on the intensity of the luminous energy that may be legally provided by a light source.

As shown in FIG. 1A, it is not required that each light source in a light source pair lie in the same vertical plane. For example, the distance from observer 4 to light RI is slightly less than the distance to light RO. However in practice, any offset distance along the Z-axis between RI and RO, or between LI and LO is negligible relative to the hundred foot or so distance Z.

Preferably the members of each pair RI and RO, and LI and LO output approximately the same color light spectrum. Applicant believes that so doing will avoid possible detriment to salience and stimulus detectability, which secure the sensation of apparent motion.

As noted, environmental degradation can interfere with the ability of observer 4 to perceive the brake lights RI, RO, LI, LO, including without limitation rain, fog or dust in the air, or dirt on the brake lights or on the windshield of the observing vehicle, or diminished luminous energy intensity from the brake light. However, under any of these conditions, applicant believes that the advantages resulting from the M cell stimuli presented by the present invention will continue to exist if not actually improve. These advantages result from the resistance of M cells, with their low acuity, to the effects of impoverished optics.

Figure 1B:
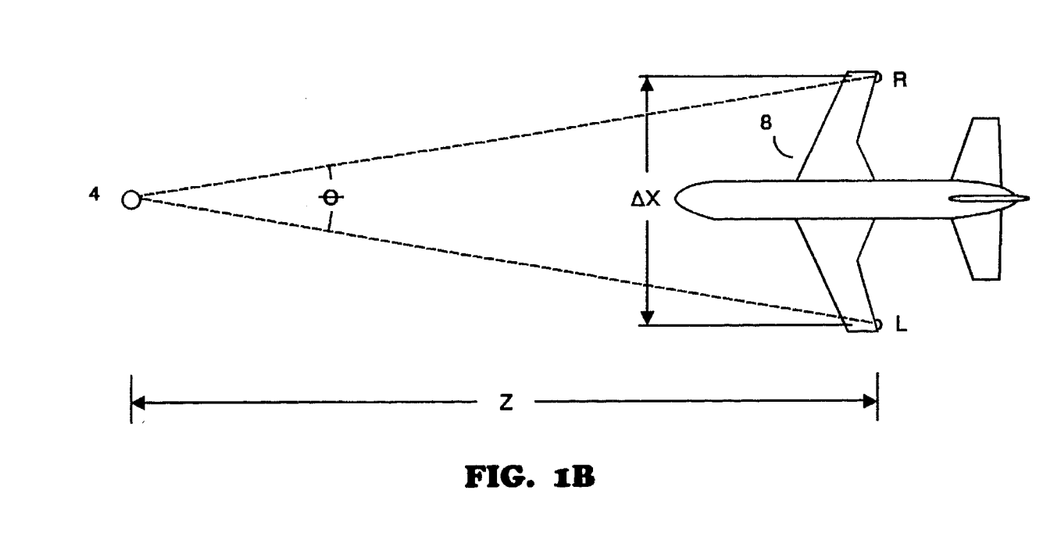
FIG. 1B is a plan view of an aircraft equipped with a strobe light on each wing-tip, according to the present invention.

Of course, the perception advantages afforded by the present invention in a dynamic warning situation are not limited to ground vehicles. As shown in FIG. 1B, lights R and L may be disposed on either side of an aircraft 8, fixed wing or otherwise. In FIG. 1B, observer 4 may be the pilot of an oncoming aircraft, or may be a ground observer.

Because of the greater velocity associated with high speed aircraft, e.g., perhaps 600 mph versus 55 mph for a motor vehicle, the distance Z at which it is important to observe aircraft 8 will be increased. If observer 4 and aircraft 8 are each closing towards each other at 600 mph, at the combined speed of 1,200 mph, a separation distance of about 18,000' (5.5 km) will be traversed in only 10 seconds. Assuming that 10 seconds represents the time wherein evasive action must be taken by aircraft 8 and/or observer 4, $Z \approx 18{,}000'$ (5.5 km). Thus, $\Delta X$ will be in the range of about 25' to about 162' (7.6 m to about 49 m). As shown in FIG. 1B, this range of $\Delta X$ readily permits locating a gas discharge strobe light (L or R) on or adjacent each wing-tip. At closer closing distances, the performance present in conventionally operated strobe light systems is retained, and at such distances the present invention loses nothing to conventional systems.

Aviation regulations require wing-tip lights to pulse continuously, flashing perhaps twice per second. According to the present invention, light L would flash on briefly (e.g., $T1 \approx 0.5$ µs or less, depending upon the luminous energy intensity from the light source), extinguish whereupon after time T2, light R would turn on for time T3. Since lights R and L preferably are identical, which promotes ease of maintenance and supply, $T3 \approx T1$. After time T3, both lights were remain off for time T4.

Because it is necessary to preclude the perception of an overlap, T2 would be in the range $10\text{ ms} \leq T2 \leq 150\text{ ms}$, since lights R and L are high speed devices. Depending upon the repetition rate duty cycle required by applicable regulation, T4 would be in the range of perhaps 400 ms to 900 ms.

To observer 4, the perception would be as if aircraft 8 were beckoning observer 4 to avoid collison by passing to the right. Of course, if applicable regulation dictated that oncoming aircraft pass to the other side, light R would be turned on first for time T1, and after an interval T2, light L would be turned on for time T3, and after an interval T4 the cycle would be repeated continuously. Thus, the present invention provides the additional benefit of conveying heading information to an observer.

As was the case for the embodiment of FIG. 1A, visual spectrum radiation from the wing will present stimuli primarily to an observer's M cells. As a result, observer 4 will more rapidly perceive and respond to the presence of aircraft 8, a response assisted by the looming image created by the "inward-to-outward" sweep of the wing lights.

Figure 1C:
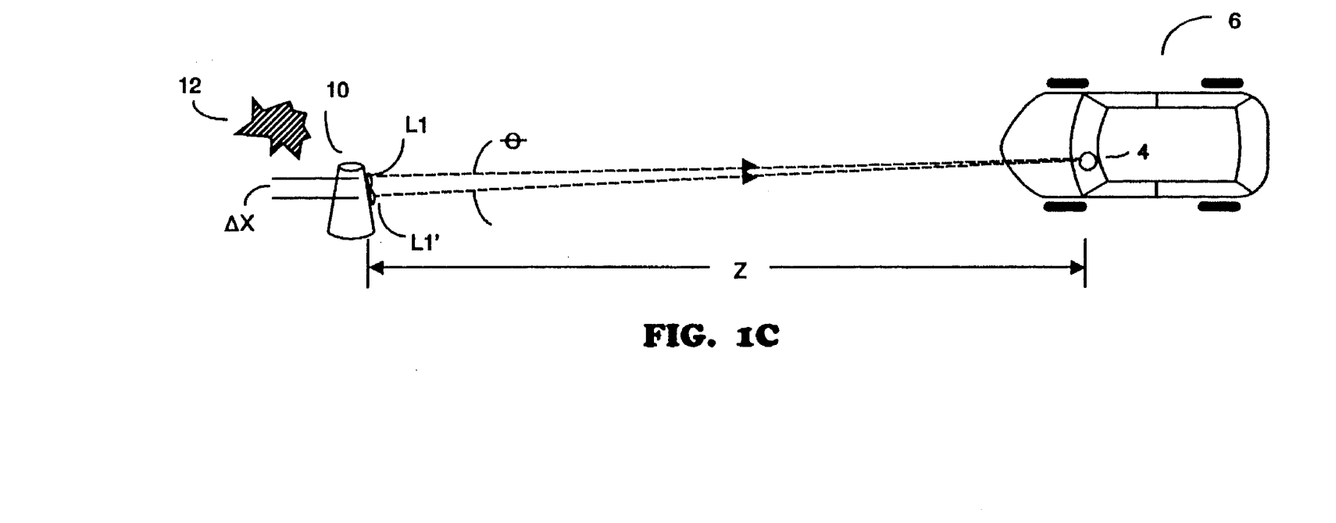
FIG. 1C depicts a stationary hazard warning device, according to the present invention.

As shown by FIG. 1C, the present invention may also be used to warn of stationary hazards. For example, a support 10 on which are mounted two lights L1, L1' may be placed near a hazard 12 (perhaps a hole in the roadway), to warn an observer 4 (perhaps an operator of a motor vehicle 6). Lights L1 and L1' are preferably spaced apart a distance $\Delta X$ that is $Z\tan\theta$. In a motor vehicle application, where Z is perhaps 100', the separation distance will be in the range 1.7" to 10.5" (4.3 cm to about 26.6 cm). Of course, L1 and L1' may be spaced apart horizontally, vertically or at some intermediate angle.

If desired, a plurality of spaced apart light pairs could be used. Such plurality can be arranged in a bulls eye configuration, the light pairs being operated to present an "inward-to-outward" sweeping pattern. Adjacent pairs of lights, e.g., L1, L1' would be operated with L1 on for time T1 and then turned off for time T2 after which L1' is turned on for time T3 and then turned off for time T4, after which L1 is turned on for time T1, and so forth. If the lights are high intensity strobe devices, $T1 \approx T3 \approx 1$ µs or so (depending upon the specific model light), $5\text{ ms} \leq T2 \leq 150\text{ ms}$, with T4 being whatever interval is necessary to provide a desired repetition duty cycle. If, however, incandescent lights were used for L1, L1', $T1 \approx T3 \approx 5$ ms to 50 ms, with about 10 ms preferred, T2 could be essentially zero (e.g., µ1 µs, if desired) or as long as perhaps 50 ms, and T4 would again be whatever interval of time is necessary to achieve a desired repetition duty cycle.

Of course support 10 could in fact be a pylon or tower adjacent an airport or near aircraft flight paths. In such embodiment, L1 could be turned on for time T1, then off for time T2, after which L1' is turned on for time T3, and after a duration T4, L1 is again turned on, to continuously repeat the pattern. This pattern would create a image that is perceived as sweeping from top-to-bottom, thus enabling pilots to readily perceive the orientation to ground. A series of such supports 10 could be placed adjacent the left and right sides of airport runways, to assist pilots in landing, especially under veiling weather conditions. One useful embodiment, for example, might orient L1 and L1' not vertically, but at 45° relative to the ground, as if pointing downward to the runway. By activating first L1 and then L1', a sweeping motion pointing 45° toward the runway would result.

Figure 1D:
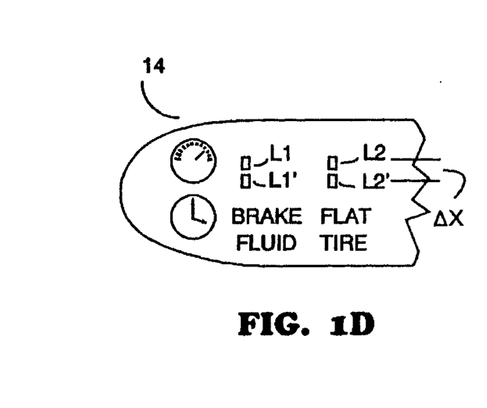
FIG. 1D depicts a non-dynamic warning light, according to the present invention.

As shown in FIG. 1D, non-dynamic warning lights can also be implemented according to the present invention, to hasten an observer's viewing the lights and recognizing the warning. For example, a motor vehicle dashboard 14 may include LED pairs L1, L1' that provide a warning, e.g., "no brakes" (possibly due to sudden loss of brake fluid), and perhaps also include LED pairs L2, L2' that provide a different warning, e.g., "flat tire" Because the critical distance Z (measured in FIG. 1D in an axis orthogonal to the plane of the figure) may be less than about 2' (61 cm), the distance separating L1 and L1' and separating L2 and L2' will be relatively small, e.g., less than about 0.2" (0.51 cm).

Preferably the LEDs are operated in a sequence, such as above described with respect to the hazard warning environment of FIG. 1C. For example, to capture the observer's attention and direct his or her eyes to the warning sign beneath the LEDs, L1 is turned on for time T1, whose duration depends upon the light intensity of L1. LED L1 is extinguished, and after time T2 (selected to be sufficiently long to preclude a perception of overlap, perhaps 5 ms to 150 ms), LED L1' turns on for duration T3, which duration need not be identical to T1. After time T3, L1' is extinguished and after time T4, the cycle repeats for the duration of the warned-against condition. T4 is selected to create an appropriate duty cycle. For example, if a rate of say 3 flashes per second were desired, T4 would be in the range of perhaps 300 ms.

Of course, the LED pairs may be spaced apart vertically (as shown), horizontally, or at some intermediate angle, and more than two LED pairs may be sequentially operated for each warning. For example, a "bulls-eye" pattern of concentric circles of LEDs could be provided wherein an "inward-to-outward" or perhaps "outward-to-inward" effect could be presented to stimulate the observer's M cell response. Further, L1, L1', L2, L2' may be other than LED lights, e.g., incandescent devices, in which case T1 and T3 would increase, and T2 would decrease.

Figure 1E:
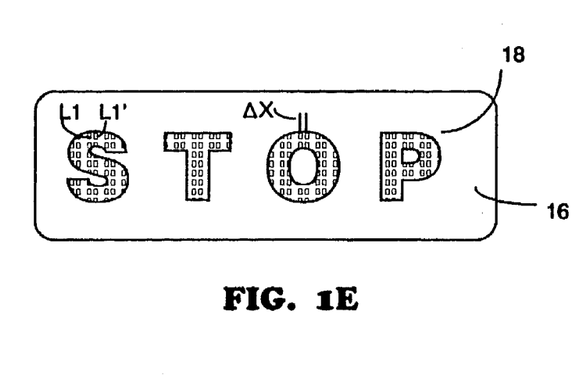
FIG. 1E depicts a stationary information sign, according to the present invention.

FIG. 1E shows yet another embodiment of the present invention, wherein a sign 16 carries a message 18, which may be a symbol, e.g., an arrow, a written warning, or perhaps a commercial advertisement. At least part of the message is represented by an array of light pairs, for example lights L1 and L1', whose pair members are sequentially activated according to the present invention. While only two lights, L1 and L1', are labelled in FIG. 1E, many such light pairs are in fact present. It is understood that L1, L1' may be spaced apart other than horizontally, as shown. L1 is turned on for time T1 and then extinguished for time T2, after which L1' is turned on for time T3 and then extinguished for time T4, after which L1 is turned on for time T1 and so on.

In FIG. 1E, the determinations of T1, T2, T3, T4 are as have been described with respect to other embodiments herein, including FIG. 1C. If incandescent lights are used, typical values may be T1≈T3≈5 ms to 50 ms, 0 ≤ T2≤150 ms, and 5 ms≤T4≤ many seconds, depending upon the desired duty cycle. It will also be appreciated that a relatively low duty cycle (e.g., a long T4) will reduce effective power consumed by the various lights, and, if the sign is battery powered, will promote battery life. Of course, if the lights in FIG. 1E are not incandescent, the values for T1, T2, T3, T4 will be determined according to the guidelines described elsewhere herein.

Figure 1F:
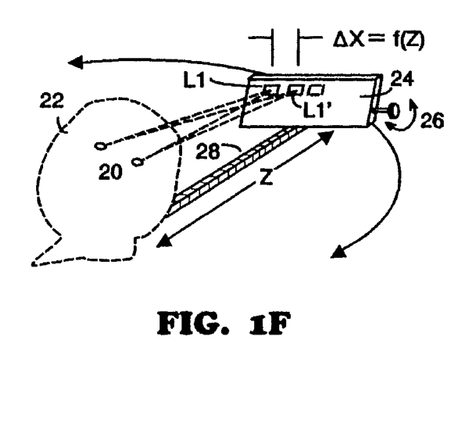
FIG. 1F depicts a perimetry test instrument, according to the present invention.

FIG. 1F shows a perimetry application of the present invention, wherein the eyes 20 of a patient 22 are tested using an M-cell stimulus generator 24 that includes spaced apart lights L1, L1'. For ease of illustration, patient 22 is shown in phantom, as though the patient's head were transparent.

As in the previous embodiments, the lights L1, L1' are spaced apart a distance $\Delta X = Z \tan \theta$. If Z≈2' (61 cm), the distance separating lights L1, L1' will be less than about 0.2" (0.51 cm). To facilitate the testing process, it is desired that Z be varied during measurement, although measurements may also be made with a fixed dimension for Z. Since $\Delta X$ should vary dynamically with changes in Z, the present invention provides a dynamic mechanism comprising elements 26 and 28 that cause $\Delta X$ to increase (or decrease) as Z increases (or decreases). This dynamic mechanism may include a track 28 extending outwardly from the patient 22, along which track generator 24 is moved, by a positioning knob 26. Internal to generator 24, as knob 26 is rotated, L1 and L1' are moved farther apart (as shown by the further-right position for L1'). Alternatively, an array of closely spaced lights L1, L2, L3 . . . Ln could be provided, wherein but two lights are sequentially activated. As Z increases, the lights chosen to be sequentially activated are lights farther apart in the array. As Z decreases, the lights chosen to be sequentially activated would be lights closer together within the array.

Because the mechanical design of track and knob repositioning mechanisms is known, as is the design of circuitry to activating chosen lights in an array, further details for varying $\Delta X$ as a function of Z are not presented herein.

In practice, generator 24 is moved left and right, and up and down to help a medical practitioner determine the outer perimeter of patent 22's field of vision, as well as vision within the perimeter. As generator 24 is being moved, lights L1, L1' are flashed, preferably using a T1, T2, T3, T4 sequence, wherein T1, T2, T3 and T4 are selected according to the guidelines described earlier herein. For example, if LED lights are used, each time interval may be in the range of about 5 ms to about 50 ms. The rays emanating from the lights thus flashed primarily stimulate the patent's M cells. Because some diseases including glaucoma are known to first affect M cell response, stimuli from generator 24 can be used to test for the onset of glaucoma.

Figure 2A:
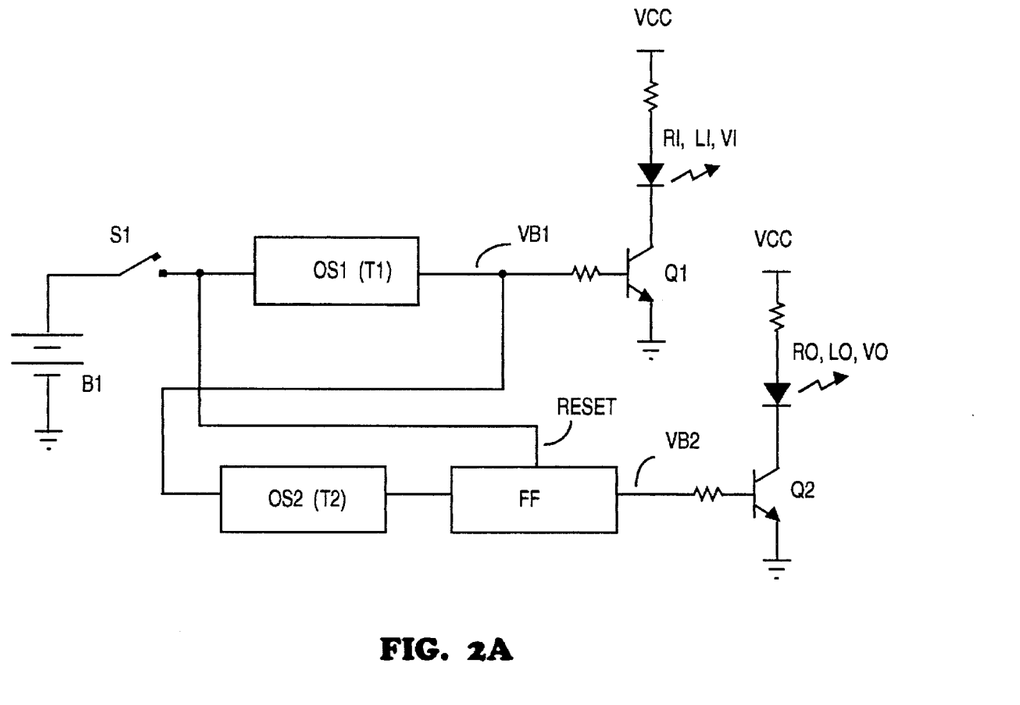
FIG. 2A is a generic depiction of an electronic switch for actuating the brake light embodiment of FIG. 1A.

Those skilled in the art of circuit design will appreciate that there are many ways to implement the above embodiments. FIG. 2A, for example, is a simplified diagram depicting activation of brake lights RI, LI immediately upon braking for a duration T1, and then after a duration T2, activating brake lights RO, LO for the duration of the braking action. If additional light pairs such as VI, VO are present, the innermost lights in such pairs are activated simultaneously with RI, LI, and the outermost lights in such pairs are activated simultaneously with RO, LO, as shown in FIG. 2A.

Figure 2B:
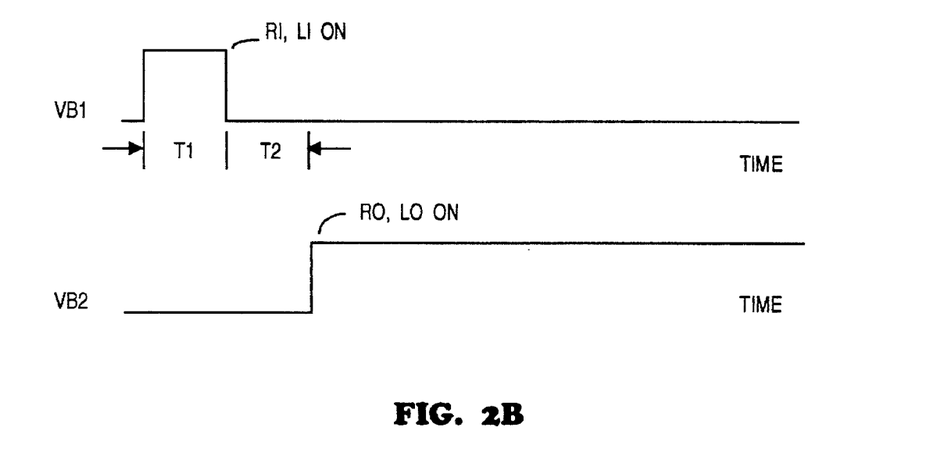
FIG. 2B depicts input timing signals for the brake light embodiment of FIGS. 1A and 2A.

In FIG. 2A, S1 represents the brake switch, which upon activation by a brake pedal couples battery voltage B1 to the braking circuit. OS1 denotes a first one-shot or monostable, whose output is a pulse shown in timing diagram FIG. 2B. The OS1 output pulse is denoted VB1, and may be coupled as the base drive to a transistor Q1 that activates R1, LI when Q1 turns on. The trailing edge of VB1 may be coupled to the input of a second one shot, OS2, that outputs a pulse having width T2.

As has been described, if RI, LI, RO, LO are incandescent, T2 may in fact be zero, which in practice may be 1 µs or substantially less, depending upon the switching speed of the transistors used. The second edge of T2 may then be used to trigger a flipflop FF whose output goes high after time T2 and remains high until reset when the motorist's foot is removed from the brake pedal, causing S1 to open. The flipflop output is coupled to a transistor Q2 that activates lights RO, LO.

It is understood that FIG. 2A is simplified in that circuitry required to "de-glitch" the switch S1 is not shown. Of course, the lights need not be LEDs as shown, and Q1 and Q2 need not be bipolar transistors. Further, the VB2 timing signal shown in FIG. 2B may be generated without using a flipflop, for example, by logically combining the output of S1, T1 and T2. Further, one-shots may be replaced with circuitry that includes a relatively high frequency clock, digital counters and reset components. The clock signal is counted for whatever digital count represents a desired interval, e.g., T1, after which the counter output is used to latch a digital gate, whose output will be a pulse of duration T1. Such techniques are well known in the art of digital circuit design and will not be described further herein.

Figure 3A:
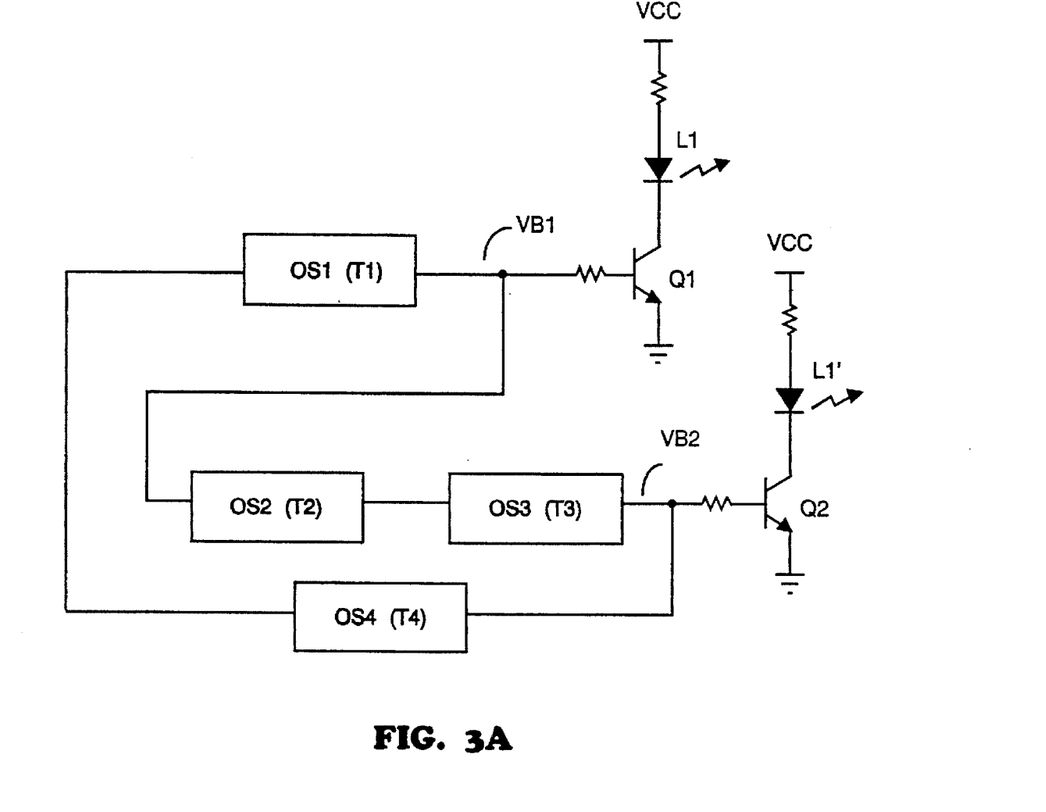
FIG. 3A is a generic depiction of an electronic switch for actuating a flashing light embodiment, according to the present invention.

FIG. 3A is a generic depiction of an oscillator comprising four one-shots OS1, OS2, OS3, OS4, that respectively create pulse widths of time duration T1, T2, T3, and T4. It is understood that FIG. 3A is somewhat simplified, and does not depict, for example, components that ensure oscillation. OS1 outputs a pulse that drives transistor Q1, energizing light L1 for a pulse duration of time T1. The VB1 pulse is also coupled as input to OS2 whose output is a pulse of duration T2. The second edge of the T2 pulse then triggers OS3 those output VB2 drives Q2. Thus, Q1 turns off and after a duration T2, Q2 turns on and energizes light L1' for a duration T3. The second edge of VB2 may then be coupled to the input of OS4. The second edge of OS4 may be coupled as input to OS1, such that when Q2 turns off, after an interval T4, Q1 will turn on, thus continuing the cycle.

Figure 3B:
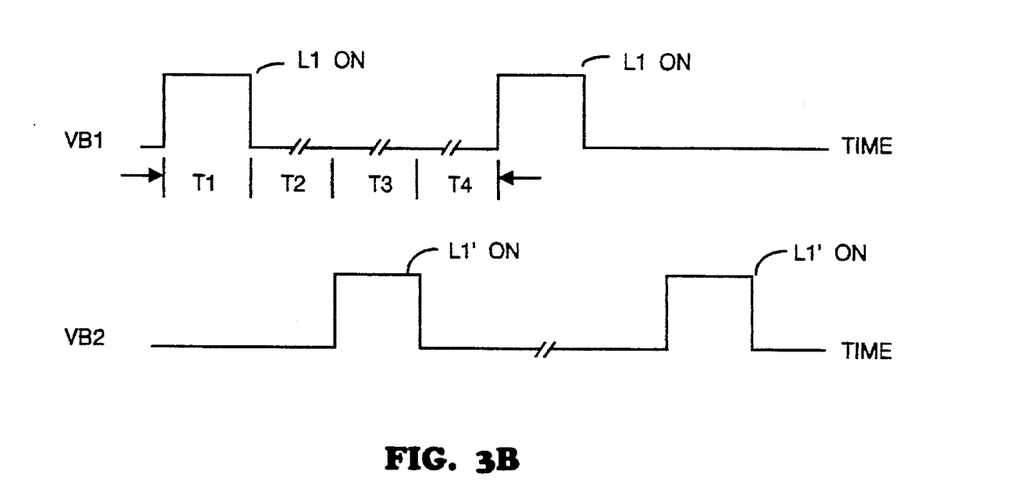
FIG. 3B depicts input timing signals for the switch embodiment of FIG. 3A.

It is again to be understood that FIG. 3A is intended to be generic, and that suitable waveforms for activating L1 and L1' may be generated in alternative ways. FIG. 3B depicts the VB1, VB2 drive signals produced by the circuit of FIG. 3A.

Modifications and variations may be made to the disclosed embodiments without departing from the subject and spirit of the invention as defined by the following claims.

What is claimed is:

1. A braking light system for a vehicle, comprising:
   first and second pairs of spaced-apart lights disposed on said vehicle, each of said pairs including an innermost light and an outermost light;
   means, coupled to a brake switch of said vehicle and to said lights, for activating at the onset of braking said innermost light of each of said pairs for a time T1, wherein 1 µs≦T1≦50 ms; for then extinguishing said innermost light of each light pair and after a time T2, wherein 0≦T2≦100 ms, then activating said outermost light of each of said pairs for the duration of braking.

2. The system of claim 1, wherein the innermost and outermost light of at least one of said pairs are spaced apart a distance equivalent to about 1 minute to about 60 minutes of visual arc at a viewing distance from said lights whereat a viewer should observe said lights.

3. The system of claim 2, wherein said viewing distance is approximately 100 feet.

4. The system of claim 1, wherein the innermost and outermost light of at least one of said pairs are spaced apart a distance ranging from about 0.4" (0.9 cm) to about 21" (53.3 cm).

5. The system of claim 1, further including:
   a third pair of spaced-apart lights, disposed on said vehicle, including an innermost light and an outermost light disposed along an axis not parallel to an axis defined by either of said first and second pairs of spaced-apart lights;
   said innermost light of said third pair being coupled to said means for activation simultaneously with said innermost light of said first and second pairs, and said outermost light of said third pair being coupled to said means for activation simultaneously with said outermost lights of said first and second pairs.

6. The system of claim 1, wherein said means for activating and extinguishing includes an electronic circuit.

7. The system of claim 1, wherein upon activation each of said lights outputs a substantially same color light spectrum.

8. A braking light system for a vehicle, comprising:
   first and second pairs of spaced-apart lights, each of said pairs including an innermost light and an outermost light disposed on said vehicle;
   a third pair of spaced-apart lights including an innermost light and an outermost light disposed on said vehicle along an axis not parallel to an axis defined by either of the first and second pairs of spaced-apart lights;
   means, coupled to a brake switch of said vehicle and to said lights, for activating at the onset of braking the innermost light of each of said pairs for a time T1, wherein 1 µs≦T1≦50 ms; for then extinguishing said innermost light of each light pairs and after a time T2, wherein 0≦T2≦100 ms, then activating said outermost light of each of said pairs for the duration of braking.

9. The system of claim 8, wherein the innermost and outermost light of at least one of said pairs are spaced apart a distance equivalent to about 1 minute to about 60 minutes of visual arc at a distance from said lights whereat a viewer should observe said lights.

10. The system of claim 9, wherein said distance is approximately 100 feet.

11. The system of claim 8, wherein the innermost and outermost light of at least one of said pairs are spaced apart a distance ranging from about 0.4" (0.9 cm) to about 21" (53.3 cm).

12. The system of claim 8, wherein said means for activating and extinguishing includes an electronic circuit.

\* \* \* \* \*